United States Patent

Aloy et al.

[11] Patent Number: 6,029,666
[45] Date of Patent: Feb. 29, 2000

[54] DEVICE FOR DELIVERING A VENTILATION GAS

[75] Inventors: Alexander Aloy, Klosterneuburg; Eva Schragl, Vienna, both of Austria

[73] Assignee: Alexander Aloy, Austria

[21] Appl. No.: 08/945,710

[22] PCT Filed: Apr. 30, 1996

[86] PCT No.: PCT/AT96/00086

§ 371 Date: Oct. 30, 1997

§ 102(e) Date: Oct. 30, 1997

[87] PCT Pub. No.: WO96/34643

PCT Pub. Date: Nov. 7, 1996

[30] Foreign Application Priority Data

May 2, 1995 [AT] Austria ................................. 243/95 U

[51] Int. Cl.[7] ............................. A61M 16/00; A62B 9/06
[52] U.S. Cl. ............................. 128/207.14; 128/204.18; 128/207.15
[58] Field of Search ........................... 128/203.12, 204.18, 128/205.11, 206.29, 207.14, 207.15, 207.16, 207.17

[56] References Cited

U.S. PATENT DOCUMENTS

| | | | |
|---|---|---|---|
| 3,346,011 | 10/1967 | Johannisson | 128/203.12 |
| 4,231,365 | 11/1980 | Scarberry | 128/207.15 |
| 4,261,355 | 4/1981 | Glazener | 128/204.25 |
| 4,270,530 | 6/1981 | Baum et al. | 128/207.15 |
| 4,425,914 | 1/1984 | Ray et al. | 128/203.12 |
| 4,537,188 | 8/1985 | Phuc | |
| 4,747,403 | 5/1988 | Gluck et al. | 128/204.21 |
| 4,838,259 | 6/1989 | Gluck et al. | 128/204.21 |
| 4,967,743 | 11/1990 | Lambert | 128/207.16 |
| 5,029,580 | 7/1991 | Radford et al. | 128/207.14 |
| 5,333,606 | 8/1994 | Schneider et al. | 128/205.24 |
| 5,343,857 | 9/1994 | Schneider et al. | 128/200.23 |
| 5,438,982 | 8/1995 | MacIntyre | 128/207.14 |
| 5,813,401 | 9/1998 | Radcliff | 128/205.24 |

FOREIGN PATENT DOCUMENTS

| | | | |
|---|---|---|---|
| 0 080 155 | 6/1983 | European Pat. Off. | |
| 0149722 | 7/1985 | European Pat. Off. | 128/204.18 |
| 0 234 736 | 9/1987 | European Pat. Off. | |
| 90/14 852 A1 | 12/1990 | European Pat. Off. | |
| 0153991 | 9/1995 | European Pat. Off. | 128/204.18 |
| 2 033 759 | 3/1980 | United Kingdom | |

Primary Examiner—John G. Weiss
Assistant Examiner—Joseph F. Weiss, Jr.
Attorney, Agent, or Firm—Nixon & Vanderhye P.C.

[57] ABSTRACT

A device for delivering a ventilation gas including a T-connector including a cross member adapted to carry a ventilation gas and a tubular stem extending substantially perpendicularly from the cross member; and a plurality of tubes each having a cross section smaller than a cross section of the tubular stem extending transversely through the cross member, and extending through and within the tubular stem, wherein remote ends of the plurality of tubes terminate beyond the tubular stem; and further wherein at least two of the plurality of tubes carry pulsating pressure gases of different frequencies.

8 Claims, 1 Drawing Sheet

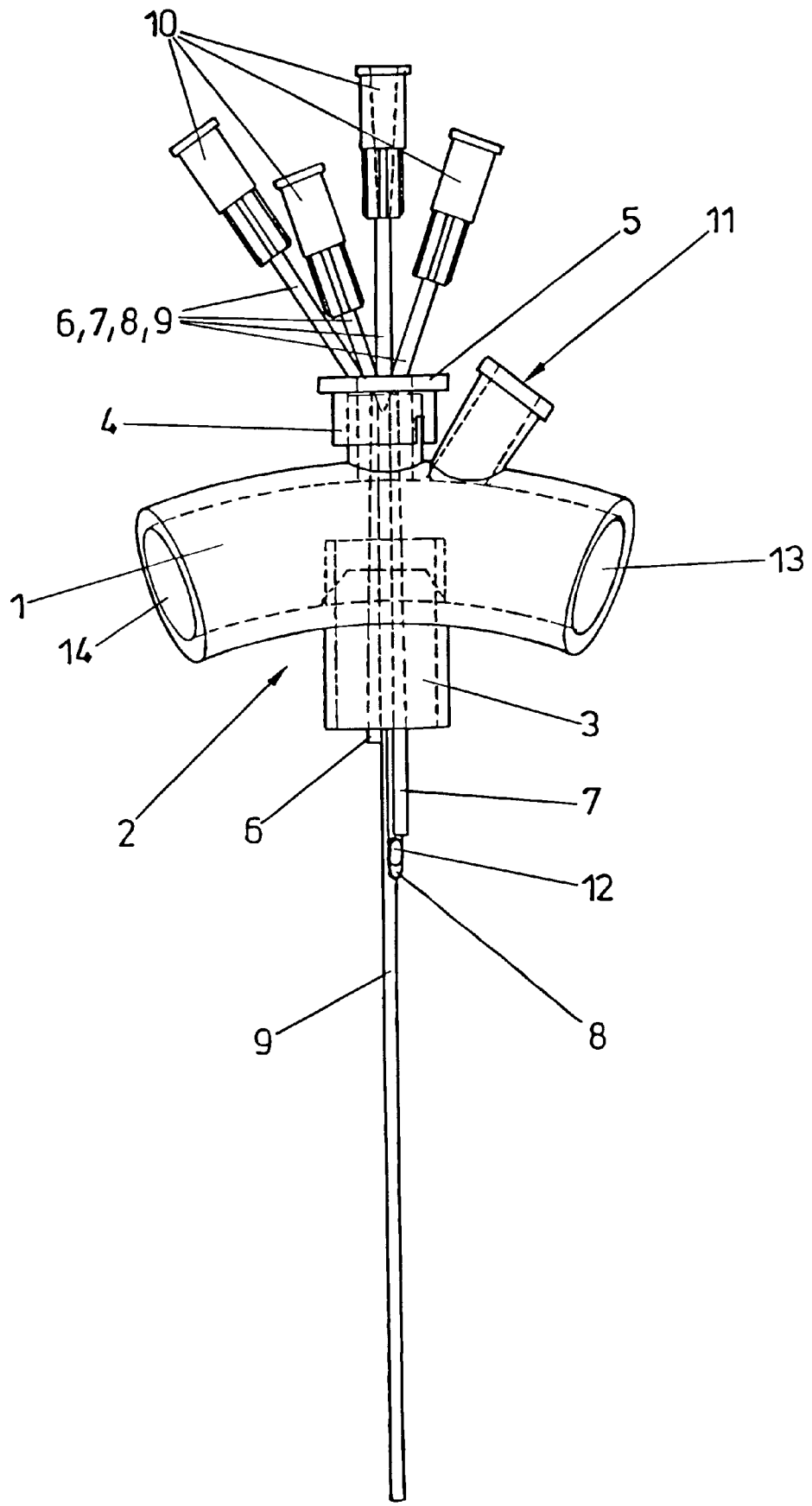

DEVICE FOR DELIVERING A VENTILATION GAS

TECHNICAL FIELD

The invention relates to a device for delivering a ventilation gas, comprising a T-connector having a T-bar and a tubular stem, with a ventilation gas flowing transversely through the T-bar.

BACKGROUND

ARDS (adult respiratory distress syndrome) is a lung failure in human adults, caused by multiple factors and characterized by a serious disorder of the gas exchange in the lung. Treatment of such a respiratory insufficiency is effected by means of mechanical artificial ventilation. There have been repeated attempts for years to administer a ventilation gas into the lung by means of a ventilation tube via a jet nozzle (jet ventilation) having a small cross section at a high initial pressure and a high respiratory frequency (100–1500/min).

SUMMARY OF THE INVENTION

This invention aims at further developing a device of the initially defined kind which will ensure, simultaneously with basic respiration, 1) a sufficiently high peak pressure or pressure plateau brought about by a low respiratory frequency at a high initial pressure; and 2) a base filling with air provided during expiration, with the final expiratory pressure plateau, produced by a high respiratory frequency at a likewise high initial pressure, in order to safely prevent the lung from collapsing. At the same time, the device according to the invention also is to enable further functions, for example, ensuring the safe measurement of the respiratory pressure generated by the gas mixtures in the lung. Finally, the invention seeks to render feasible the realization of additional therapeutic or diagnostic measures without changing the device.

Accordingly, the configuration according to the invention includes a T-connector having a T-bar or cross member and a tubular stem part which extends perpendicularly away from the T-bar. An opening is provided in the T-bar, surrounded by a bushing, opposite the tubular stem part, i.e., the opening and the tubular stem part are coaxial. An open lid is adapted to be locked to the bushing. With this arrangement, a plurality of tubes having clear cross sections smaller than the clear cross section of the T-connector tubular stem part, extend through the opening and through the tubular stem part, transverse to the T-bar. At least two of the tubes are fed with pulsating pressure gases of different frequency.

By employing a plurality of tubes having smaller clear cross sections, it has become feasible to not only provide ventilation gas having a high predetermined pressure and predetermined respiratory frequency, but, at the same time, impress varying respiratory frequencies via various tubes differing from one another. Using two different respiratory frequencies, on the one hand, safeguards the respective basic filling during expiration (positive final expiratory pressure) thereby preventing the lung from collapsing completely (high respiratory frequency) and, on the other hand, allows for appropriate inflation (inspiratory pressure plateau) during inspiration (low respiratory frequency). By means of further such tubes having small clear cross sections, the respiratory pressure in the lung produced by the gas3 mixtures may be measured safely at a point suitable therefor, wherein for instance, isotonic saline solution or therapeutically active substances may simultaneously be injected and atomized through an additional tube of this kind. Advantageously, the device is further developed in a manner that the tubes have different lengths in the axial direction and the tube having the largest axial length is corrected with a pressure measuring means. By measuring the pressure via the tube having the largest axial length, the pressure prevailing close to the lung is detected, thereby actually allowing for the safe recording of the respiratory pressure.

In order to safeguard conditions that are beneficial to therapeutically active substances or to respiration, the configuration advantageously is devised such that one tube is designed with a substantially radial outlet nozzle and a shorter tube opens in the vicinity of said outlet nozzle. Saline solution may be conducted through the radial outlet nozzle and atomized by means of the neighboring shorter tube. The configuration in this case advantageously is devised such that the tube impressed with a higher gas pulse frequency opens near the radial outlet nozzle and is designed to be longer in the axial direction than the tube for pulsating pressure gas of lower frequency, thereby ensuring particularly good atomization.

In order to render feasible additional diagnostic measures and, in particular, allow for the :realization of, for instance, a bronchoscopy, the configuration advantageously is devised such that a closeable funnel opens into the T-connector.

Particularly simple assemblage of the device according to the invention as well as simple mounting, may be achieved in that the tubes are fixed in an open, socket-like lid which can be tightly locked with the T-connector bushing. In one example, the lid is capable of being locked by means of a conventional bayonet joint within the bushing. Such a lid may readily be put on the corresponding opening and locked, and the manufacture of the lid so as to carry the plurality of tubes being feasible in a particularly simple manner.

In order to be able to connect to the various tubes the respective gas or liquid sources in a simple and standardized manner, the configuration advantageously is devised such that the tubes carry standard fittings, such as, for instance, Luer connections, on the ends located above the T-bar of the T-connector.

A particularly simple and operationally safe device may be provided in that four tubes are fixed in the socket piece or lid, whose overall cross section is smaller than 25%, preferably smaller than 10%, of the clear cross section of the T-connector tubular stem part extending normal to the T-bar, wherein such a device allows for the spraying of saline solution in addition to the continuous monitoring of the respiratory pressure and the simultaneous operation at high and low frequencies, for instance, with a ventilation gas under a pressure of about 1.5 to 3 bars, for instance 2 bars.

In an advanced configuration, the functional safety of the device according to the invention advantageously is further enhanced in that the otherwise unprotected proximal tube sections are designed to be reinforced, which may, for instance, be obtained by means of spiral springs arranged coaxial with the tubes, thereby increasing the buckling and torsional strengths. The thus obtained high resistance of the tube walls will take effect, in particular, if the device is exposed to elevated stress in case of emergency.

In the following, the device according to the invention will be explained in more detail by way of an exemplary embodiment schematically illustrated in the drawing.

BRIEF DESCRIPTION OF THE DRAWINGS

The Figure is a side elevation of a T-connector and tube assembly in accordance with the invention.

DETAILED DESCRIPTION OF THE DRAWINGS

Referring to the drawing, a T-connector 1 in accordance with the invention includes a T-bar or cross member 2 and a tubular stem 3 which extends perpendicularly from the: T-bar 2. A bushing 4 provides an opening in the T-bar, opposite the tubular stem 3, such that the bushing 4 and the opening defined thereby are coaxial with the tubular stem 3.

An open, socket-like lid 5 is placed on the bushing 4, carrying four tubes of relatively small cross section 6, 7, 8 and 9. These tubes extend through the bushing 4 and the tubular stem 3 as shown in the Figure, with remote ends of the tubes terminating beyond the stem. A luer connection 10 is attached to each of the tubes 6, 7, 8 and 9.

A closeable funnel 11 is attached to, and extends away from, the T-bar, adjacent the bushing 4. This arrangement permits a bronchoscopy to be carried out. As seen in the Figure, the tubes 6, 7, 8 and 9 have different axial lengths. Low frequency ventilation gas passes through the axially shortest tube 6.

Tube 8 has a radial outlet opening 12 near the mouth of the respectively shorter tube 7. Higher respiratory frequency ventilation gas can be introduced through tube 7 in order to atomize liquid media fed via tube 8. Tube 9, which is longest in the axial direction, serves to continuously perform pressure measurements.

In use, a ventilation gas transverse flow is connected to the T-bar 1, specifically, a moistened and heated gas is introduced through the 13 and expiration being effected through opening 14.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

We claims:

1. A device for delivering a ventilation gas comprising a T-connector including a cross member adapted to carry a ventilation gas and a tubular stem extending substantially perpendicularly from said cross member, a closeable funnel opening into said cross member; and a plurality of tubes e each having a cross section smaller than a cross section of the tubular stem extending transversely through said cross member, and extending through and within said tubular stem, wherein remote ends of said plurality of tubes terminate beyond said tubular stem; and further wherein at least two of said plurality of tubes carry pulsating pressure gases of different frequencies.

2. A device according to claim 1, wherein said plurality of tubes have different axial lengths and further wherein a first of said plurality of tubes which has the largest axial length connected with a pressure measuring means.

3. A device according to claim 1, wherein a second of said plurality of tubes is provided with a substantially radial outlet nozzle, and a third tube shorter than said second tube opens in the vicinity of said outlet nozzle.

4. A device according to claim 3, wherein the third tube is impressed with a higher gas pulse frequency and is longer in the axial direction than a fourth tube of said plurality of tubes for pulsating pressure gas of lower frequency.

5. A device according to claim 1, wherein said plurality of tubes are fixed in a lid capable of being tightly and releasably locked with said cross member.

6. A device according to claim 5, wherein said lid is adapted to be locked within an opening in said cross member, said opening aligned with said tubular stem.

7. A device according to claim 6, wherein said plurality of tubes carry fittings on ends located above the cross member.

8. A device according to claim 1, wherein said plurality of tubes have a combined cross section at least 25% smaller than the cross section of the tubular stem.

* * * * *